(12) United States Patent
Takada

(10) Patent No.: US 7,097,851 B1
(45) Date of Patent: Aug. 29, 2006

(54) ORAL FORMULATION FOR GASTROINTESTINAL DRUG DELIVERY

(76) Inventor: Kanji Takada, 618-2, Gokoumachidori Gojoagaru Azuchi-cho, Shimogyo-ku, Kyoto-shi, Kyoto 600-8040 (JP)

( * ) Notice: Subject to any disclaimer, the term of this patent is extended or adjusted under 35 U.S.C. 154(b) by 0 days.

(21) Appl. No.: 09/831,901

(22) PCT Filed: Nov. 26, 1999

(86) PCT No.: PCT/JP99/06602

§ 371 (c)(1),
(2), (4) Date: Aug. 7, 2001

(87) PCT Pub. No.: WO00/32172

PCT Pub. Date: Jun. 8, 2000

(30) Foreign Application Priority Data

Nov. 27, 1998 (JP) ............................. 10-353966
Sep. 21, 1999 (JP) ............................. 11-266433

(51) Int. Cl.
A61F 13/00 (2006.01)
A61K 9/20 (2006.01)
A61K 9/24 (2006.01)
A61K 9/28 (2006.01)
A61K 9/48 (2006.01)

(52) U.S. Cl. .................. 424/435; 424/464; 424/465; 424/472; 424/474; 424/451

(58) Field of Classification Search ............. 424/463, 424/484, 486, 488, 443, 444, 400, 451, 435, 424/464, 465, 472, 474
See application file for complete search history.

(56) References Cited

U.S. PATENT DOCUMENTS 4,765,983 A * 8/1988 Takayanagi et al. ........ 424/434
4,767,627 A * 8/1988 Caldwell et al. ............ 424/400
5,236,713 A 8/1993 Wato et al.
5,350,741 A 9/1994 Takada
5,637,319 A 6/1997 Takada
5,686,105 A * 11/1997 Kelm et al. ................. 424/452
5,700,478 A * 12/1997 Biegajski et al. ........... 424/434
6,086,869 A * 7/2000 Uyama et al. ............. 424/85.4
6,194,000 B1 * 2/2001 Smith et al. ................ 424/458
6,231,888 B1 * 5/2001 Lerner et al. ............... 424/463

FOREIGN PATENT DOCUMENTS

WO          98/24412          6/1998

OTHER PUBLICATIONS

"Pharmaceutical Research", vol. 2, pp. 397-405 (1995).
Takada, "Pharm. Tech. Japan", pp. 1299-1307 (1988).
Takada, "Pharm. Tech. Japan", pp. 512-515, 518-521 (1991).
Takada, "Pharm. Tech. Japan", pp. 1335-1344 (1995).

(Continued)

Primary Examiner—Isis Ghali
(74) Attorney, Agent, or Firm—Greenblum & Bernstein, P.L.C.

(57) ABSTRACT

An oral formulation for gastrointestinal drug delivery which comprises an adhesion site-controlling layer for attaching the formulation to the selected site in the digestive tract, a drug-carrying layer for containing a drug and an adhesive and a protecting layer for protecting the drug in the drug-carrying layer, wherein the drug-carrying layer exists between the protecting layer and the adhesion site-controlling layer, and the adhesion site-controlling layer may attach to the protecting layer. The formulation can improve bioavailability of drugs which have low bioavailability.

22 Claims, 5 Drawing Sheets

OTHER PUBLICATIONS

Ko et al., Nippon Rinsho, "Japan Clinicals", pp. 595-600 (1998), (with English language abstract).
Ohyama Takao et al., Ishoku [Transplantation], vol. 34, No. 4, pp. 174-185 (1999), (with English language abstract).
Takada, "Pharm. Tech. Japan", 1995, pp. 903-913.
Takada, "Pharm. Tech Japan", 1995, pp. 1035-1042.
Oral Protein/Peptide Delivery Technology, Ver 1.2, Mar. 1, 2002, Gastrointestinal Mucoadhesive Patch System (GI-MAPS™), pp. 1-6.

* cited by examiner

ORAL FORMULATION FOR GASTROINTESTINAL DRUG DELIVERY

TECHNICAL FIELD

The present invention relates to an oral formulation for gastrointestinal drug delivery. More specifically, the present invention relates to an oral formulation for gastrointestinal drug delivery to improve the bioavailability of drugs that have a low bioavailability due to a low absorption in the digestive tract.

BACKGROUND ART

Low bioavailability of drugs after oral administration is considered to be caused by the following factors. (1) In oral administration of formulations such as common tablets and capsules, the concentration gradient of the drug between the digestive lumen and the blood increases immediately after release of the drug from the oral formulation, but rapidly decreases while the formulation moves to the lower part of the digestive tract, which gives a disadvantage to the drug absorption conditions. (2) Drugs such as furosemide are absorbed from the limited absorption site of the upper part of the small intestine (the so-called window effect), and common formulations of such drugs cannot exhibit satisfactory bioavailability after passing through the absorption site. (3) Drugs of protein or peptide are subjected to drastic hydrolytic degradation by digestive enzymes secreted to the digestive tract, whereby the bioavailability is reduced to only a few percentage. (4) HIV protease inhibitors such as ritonavir, saquinavir, indinavir and nelfinavir are, after absorbed from the digestive tract, actively excreted by excretory proteins such as P-gp expressed on the epithelial cell membrane of the intestinal tract.

In order to improve low bioavailability of drugs caused by the window effect, Akiyama et. al. developed mucosa adhesive granule formulations (Pharmaceutical Research, vol. 12, pp. 397–405, 1995).

As conventional techniques for improving bioavailability of protein and peptide after oral administration, with the main object of preventing hydrolytic degradation in the stomach and the small intestine, there have been developed a colon dissolvable azopolymer-coated insulin tablet by Dr. Saffran et. al., an emulsion preparation from Cortex Co., a technique for manufacturing oral formulation by Takada, a colon delivery technique, and a liposome preparation by Takada (Takada, Pharm. Tech. Japan, 1988, pp. 1299–1307; Takada, Pharm. Tech. Japan, 1991, pp. 512–52; Takada, Pharm. Tech. Japan, 1995, pp. 1335–1344; Ko et. al., Nippon Rinsho [Japan Clinicals], 1998, pp. 595–600) and the like.

DISCLOSURE OF THE INVENTION

In mucosa adhesive granule formulations, the drug molecules cannot be protected from the attack of digestive enzymes existing in the digestive tract. Also in the peptide or protein oral formulations above, it is difficult to perfectly prevent the protein or peptide from the attack of digestive enzymes in the small-intestinal lumen.

The object of the present invention is to provide an oral formulation for drug delivery (sometimes referred to as drug delivery system (DDS) formulations) which enable improvement of the bioavailability by preparing a patch preparation by using a gel-forming polymer and a water-insoluble polymer which adheres to the mucosal membrane of the digestive tract after oral administration and prevents permeation of digestive enzymes existing in the digestive tract, protecting the drug molecules in the patch preparation from the attack of digestive enzymes in the small intestine lumen, and retaining the concentration gradient over a long period of time by adhesion to the mucosal membrane.

The present inventors conducted various studies to achieve the aforementioned object, and have successfully developed an oral formulation for gastrointestinal drug delivery which comprises three layers each having a specific function. The present invention was achieved on the basis of these findings.

According to the present invention, there is provided an oral formulation for gastrointestinal drug delivery which comprises an adhesion site-controlling layer for attaching the formulation to the selected site in the digestive tract, a drug-carrying layer for containing a drug and an adhesive, and a protecting layer for protecting the drug in the drug-carrying layer, wherein the drug-carrying layer exists between the protecting layer and the adhesion site-controlling layer, and the adhesion site-controlling layer may attach to the protecting layer.

According to an embodiment of the present invention, there is provided the oral formulation for gastrointestinal drug delivery wherein each of the adhesion site-controlling layer, the drug-carrying layer and the protecting layer is in the form of film, and these three layers are laminated. In this embodiment, each of the thickness of the adhesion site-controlling layer, the drug-carrying layer and the protecting layer is preferably from 20 to 100 µm.

According to another embodiment of the present invention, there is provided the oral formulation for gastrointestinal drug delivery wherein the protecting layer is in the hemispherical form, and the drug-carrying layer exists in the inner space of the protecting layer in the hemispherical form, and wherein the adhesion site-controlling layer covers the opening part of the protecting layer in the hemispherical form. In this embodiment, the inside depth of the hemisphere is preferably from 50 to 500 µm, the inside diameter of the opening part of the hemisphere is preferably from 20 to 800 µm, and the thickness of the protecting layer and the adhesion site-controlling layer is preferably from 20 to 100 µm.

Preferably, the drug-carrying layer is a porous sheet substrate soaked with a drug, or a sheet or a film of gel or wax which contains a drug.

Preferably, the drug-carrying layer further contains one or more ingredients selected from a group consisting of absorption promoters, protease inhibitors and transporter inhibitors.

Preferably, the protecting layer is a film or capsule made of a water-insoluble polymer or wax.

Preferably, the adhesion site-controlling layer is a film made of an enteric polymer.

Preferably, the drug is a physiologically active protein or peptide.

Preferably, the drug is G-CSF, interferon or indinavir.

According to another aspect of the present invention, there is provided an oral capsule formulation which is prepared by filling the aforementioned formulation in a capsule. The oral capsule formulation is preferably an enteric capsule.

The present invention also relates to an oral formulation for gastrointestinal drug delivery which comprises an adhesion site-controlling layer for attaching the formulation to a selected site in the intestines, a drug-carrying layer containing a drug and an adhesive to attach the drug containing layer to the selected site in the intestines when the adhesion site-controlling layer dissolves at the selected site in the intestines, and a protecting layer for protecting the drug in the drug-carrying layer, the drug-carrying layer existing between the protecting layer and the adhesion site-controlling layer, the adhesion site-controlling layer may attach to the protecting layer and the adhesion site-controlling layer is a film made of an enteric polymer.

PREFERRED EMBODIMENT FOR CARRYING OUT THE INVENTION

Figure 1:
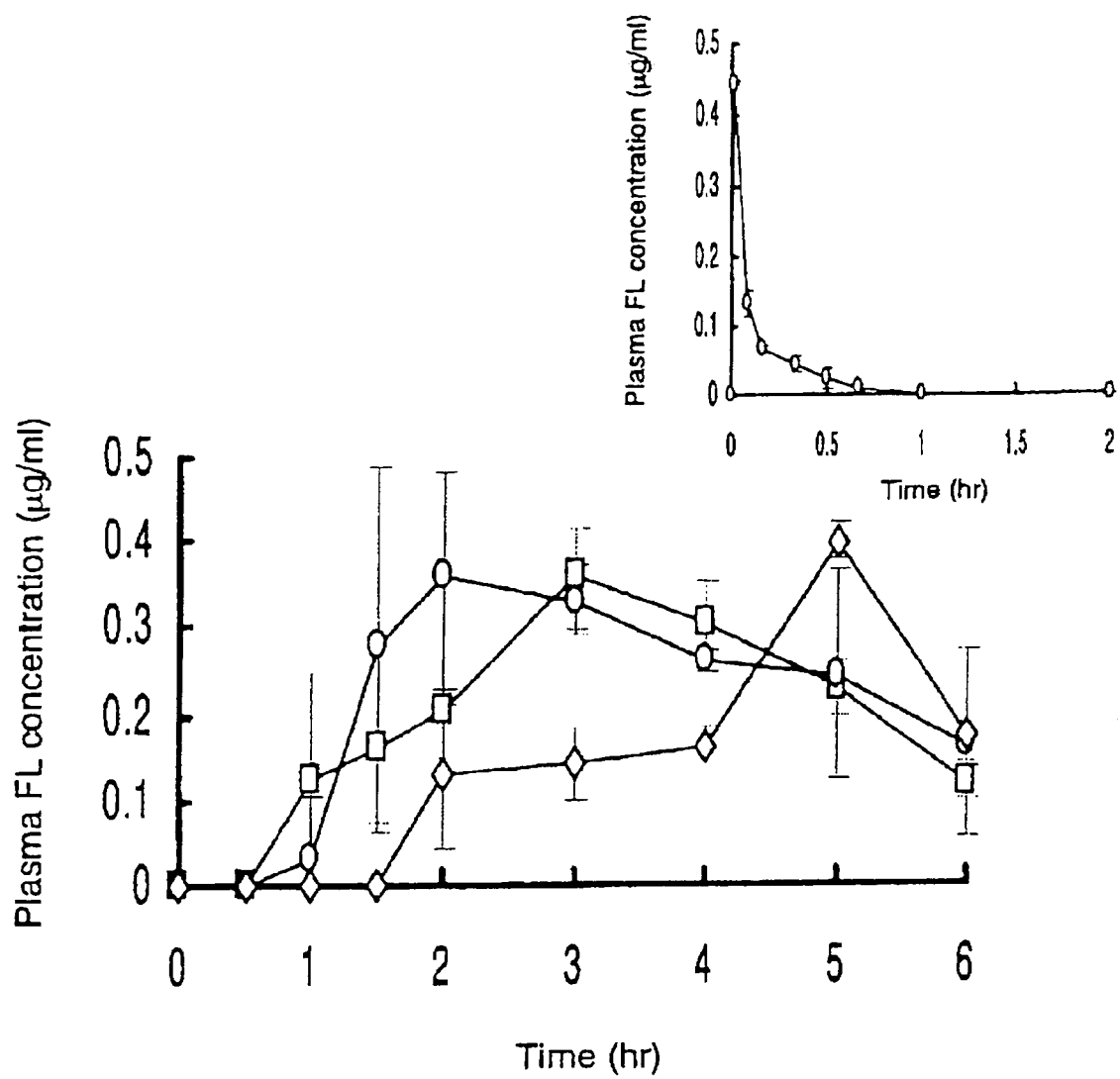
FIG. 1 shows plasma fluorescein (FL) concentration-time curves after i.v., 1 mg, and oral, 30 mg, administration of FL in gastrointestinal (GI)-mucoadhesive delivery systems to beagle dogs. In the figure, □: HP-55$^R$ system, ○: Eudrag$^R$ L100 System, and ◇: Eudrait$^R$ S100 system. Each value represents the mean ±S.E. of three or four subjects.

The oral formulation for gastrointestinal drug delivery according to the present invention is characterized in that the formulation comprises an adhesion site-controlling layer for attaching the formulation to a selected site in the digestive tract, a drug-carrying layer for containing a drug and an adhesive and a protecting layer for protecting the drug in the drug-carrying layer, and the drug-carrying layer exists between the protecting layer and the adhesion site-controlling layer, and the adhesion site-controlling layer may attach to the protecting layer.

When the formulation of the present invention is orally administered, the adhesion site-controlling layer dissolves at an unique site in the digestive tract. The site of the mucosal membrane of the digestive tract, to which the drug-carrying layer attaches, is controlled by such dissolution of the adhesion site-controlling layer at an unique site in the digestive tract. After the oral administration of the formulation, the protecting layer prevents digestive juice from permeating into the drug-carrying layer and the drug-carrying layer from releasing the drug, and also prevents digestive juice and digestive enzymes from permeating into the drug-carrying layer after the formulation attaches to the mucosal membrane of the digestive tract. The bioavailability of the drug orally administered is improved by the protection of drug molecules from the attack of digestive enzymes and the retention of the concentration gradient over a long period of time.

The adhesion site-controlling layer comprises a substance which prevents the drug from burst-releasing in the early phase and dissolves at a specific patch (adhesion) site selected in the digestive tract. Typically, the adhesion site-controlling layer is made of a pH dependent enteric polymer such as hydroxypropyl methylcellulose phathalate (HP-55$^R$), methacrylic copolymer (Eudragit$^R$ L), methacrylic copolymer-LD (Eudragit$^R$ LD) and methacrylic copolymer-S (Eudragit$^R$ S). The thickness of the adhesion site-controlling layer is generally from 20 to 100 μm, preferably from 30 to 70 μm, and more preferably from 40 to 50 μm.

The drug-carrying layer is an intermediate layer which exists between the protecting layer and the adhesion site-controlling layer. The drug-carrying layer contains a drug and an adhesive. The adhesive is used for attaching the drug-carrying layer to the mucosal membrane of the digestive tract when the adhesion site-controlling layer dissolves at a site selected in the digestive tract.

The type of the drug contained in the drug-carrying layer is not particularly limited, and is preferably those having a low bioavailability when orally administered. Those absorbed in gastrointestinal tract, especially in intestine are preferred. Examples include physiologically active protein or peptide (for example, granulocyte colony-stimulating factor (G-CSF), interferon including interferon-α, β and γ, erythropoietin, interleukins, growth hormones, calcitonin and insulin), as well as DNA or RNA including oligo- or poly-nucleotide (DNA may be in the form of plasmid), aromatic, antigen or antibody (for example, botulinum toxin) and cells (for example, pancreatic Langerhans islet). More specifically, examples include G-CSF, indinavir and interferon.

The adhesive for attaching the drug-carrying layer to the mucosal membrane of the digestive tract may be prepared by mixing a plasticizer to polymers or gums such as carboxyvinyl polymer, acrylate/octyl acrylate copolymer, 2-ethylhexyl acrylate/vinylpyrrolidone copolymer, acrylate silk-broin copolymer resin, methyl acrylate/2-ethylhexyl acrylate copolymer resin, gum arabic, poly(vinyl alcohol), polyvinylpyrrolidone, methylcellulose, polyisoprene, polyacrylate, and sodium polyacrylate, followed by kneading the mixture with water. For example, an adhesive may be prepared by kneading 0.8 g of Hiviswako$^R$ 103, 250 μl of PEG 400 and 2 ml of purified water.

When a support is used as the drug-carrying layer, examples of the support include porous substrate soaked with a drug such as polyester fiber, thin cloth, tissue paper, and synthetic paper or film made of a synthetic cellulose polymer or an enteric polymer.

When a gel layer is used as the drug-carrying layer, the gel layer may be prepared by mixing an aqueous solution of a drug, powders of a drug, or a solid dispersion of a drug, or a micro- or nano-encapsuled drug with a concentrated solution of a gel-forming polymer such as carboxyvinyl polymer. Instead of the gel layer, there may be used a hydrophilic wax layer prepared by adding a drug and an adhesive such as Hiviswako 103$^R$ to a hydrophilic wax such as polyethylene glycol 400 (PEG 400). When nano- or micro-encapsulation is applied to the drug, a use of hydroxypropyl methylcellulose phthalate (HP-55$^R$) as a nano- or microcapsule wall gives rapid release of the drug after attaching to the gastrointestinal wall.

In addition, by formulating the absorption promoter such as polyoxyethylated castor oil derivatives, capric acid and ursodeoxycholic acid etc. into the drug-carrying layer, the bioavailability of the drug can be further improved. Alternatively, by formulating protease inhibitors such as aprotinin in the drug-carrying layer, hydrolytic degradation of a peptide or protein drug can be effectively inhibited and bioavailability of the drug can also be improved. Alternatively, by formulating inhibitors of transporter like P-gp participating in the excretion of the absorbed drug (ex., verapamil and cyclosporine) to the drug-carrying layer, the bioavailability of the drug can be improved.

As explained below, the drug-carrying layer used in the present invention may be in the form of film or may exist in the inner space of the hemispherical form made of the protecting layer. When the drug-carrying layer is in the form of a film, the thickness of the film is generally from 20 to 100 µm, preferably from 30 to 70 µm, and more preferably from 40 to 50 µm.

The protecting layer (backing layer) functions for protecting the drug in the drug-carrying layer and is in the form of a film or a wall, for example a hemispheric form, which is made of a water-insoluble polymer, a wax, or a mixture thereof to inhibit permeation of the drug into the drug-carrying layer and digestive enzymes. The protecting layer may be prepared, for example, by using a water-insoluble pharmaceutical polymer such as ethylcellulose, aminoalkylmethacrylate copolymer (Eudragit RS), cellulose acetate, chitin and chitosan, or a wax such as stearic acid, stearyl alcohol, white beeswax, cacao butter, hard fat, purified shellac, polyoxyl 40 stearate, cetanol and polyoxyethyl lauryl ether. The thickness of the protecting layer is generally from 20 to 100 µm, preferably from 30 to 70 µm, and more preferably from 40 to 50 µm. When the protecting layer is in the hemispherical form, the size of the hemisphere is not particularly limited. For example, the inside depth of the hemisphere is from 50 to 500 µm, and the inside diameter (caliber) of the hemisphere is from 20 to 800 µm, preferably from 50 to 500 µm, and more preferably from 100 to 300 µm.

According to the present invention, the drug-carrying layer exists between the protecting layer and the adhesion site-controlling layer. Examples of those wherein the drug-carrying layer exists between the protecting layer and the adhesion site-controlling layer include (1) where the adhesion site-controlling layer, the drug-carrying layer and the protecting layer are in the form of film respectively, and these three layers are laminated in order (hereinafter referred to as the formulation according to the first embodiment) and (2) where the protecting layer is in the hemispherical form, the drug-carrying layer exists in the inner space of the hemispherical form, and the adhesion site-controlling layer covers the opening part of the hemisphere (hereinafter referred to as the formulation according to the second embodiment). The methods for preparing the aforementioned formulations in the first and second embodiments, which are typical examples of the present invention, will be described below in detail.

In order to prepare the formulation according to the first embodiment, a film for the protecting layer is formed by using a water-insoluble polymer or a wax mentioned above. More specifically, a water-insoluble polymer or wax is dissolved in an organic solvent such as ethanol, the resulting solution is cast in a Teflon flame, and the solvent is evaporated. For example, 550 mg of ethylcellulose and 150 µl, of triethyl citrate are dissolved in 5 ml of a mixture of methylene chloride and methanol (4:1), and the resulting solution is cast on a Teflon plate.

Next, as explained above, the drug-carrying layer is formed on the protecting layer. An adhesive may be applied on the protecting layer and then the support containing a drug is attached thereon to form the drug-carrying layer, or alternatively, a drug and an adhesive (such as gel forming polymers) may be mixed and then applied on the protecting layer.

As the adhesion site-controlling layer, a film from having from 20 to 100 µm thickness that is made of an enteric polymer as explained above may be used. For example, 225 mg of HP-55$^R$ (Shin-etsu Chemical Ind. Co. Ltd.) and 25 µl of triethyl citrate are dissolved in 5 ml of a mixture of methylene chloride and methanol (4:1), and the resulting solution is cast on a Teflon plate to form a film. As another example, a film may be used which is prepared by dissolving 225 mg of Eudragit$^R$ S100 or Eudragit$^R$ L100 and 150 µl of triethyl citrate in 5 ml of a mixture of methylene chloride and methanol (4:1) and casting the resulting solution on a Teflon plate. The formulation according to the first embodiment of the present invention may be prepared by attaching such a film on the drug-carrying layer with an adhesive and the like and cutting the three-layered film into an appropriate size. In addition, in order to prevent a leak of a drug and the like from the edges of the drug-carrying layer between the protecting layer and the adhesion site-controlling layer, it is preferred that the formulation is sealed by sprinkling a water-insoluble substance such as stearic acid fine powders.

The size of the film patch formulation is not limited so far that the formulation can be filled into a gelatin capsule or an enteric capsule made of an enteric polymer. For example, the size may be a square of 3×3 mm and a circle of 5 mm in diameter. In order to prevent adhesion or sticking of the films to each other when filled into a capsule in piles, the lubrication treatment is preferably applied by sprinkling magnesium silicate powders.

In order to prepare the formulation in the second embodiment, the protecting layer in the hemispherical form used in the present invention may be prepared by cutting minicapsules or microcapsules made of a water-insoluble polymer or a wax into half. The minicapsules or microcapsules are prepared by using a water-insoluble polymer such as ethylcellulose or Eudragit RS100 in a conventional method, and then the resulting capsules are cut at the center into two pieces, and the inside is scraped off to prepare hollow half-minicapsules or half-microcapsules in the hemispherical (bowl) form, which serves as the protecting layer. For preparing the drug-carrying layer, a drug and a gel forming polymer are mixed and filled into the half-minicapsules or half-microcapsules. The adhesion site-controlling layer may be formed by attaching a film made of an enteric polymer on the upper part of the half-minicapsules or half-microcapsules using a gel forming polymer glue so as to cap the half-capsules. Alternatively, the minicapsules or microcapsules which contain a drug and an adhesive polymer, may be prepared by using a water-insoluble polymer such as ethylcellulose or Eudragit$^R$ RS100 in a conventional method, and the resulting capsules are cut at the center into two pieces. Then, the adhesion site-controlling layer may be formed by attaching a film made of an enteric polymer on the upper part of the half-minicapsules or half-microcapsules using a gel forming polymer glue so as to cap the half-capsules.

Alternatively, in order to prepare the formulation in the second embodiment in a large amount, a film is formed by using a water-insoluble polymer or a wax in a similar manner to that in preparing the protecting layer used in the formulations in the first embodiment. The resulting film is put on a thorny object having many projections of the micron order regularly arranged such as a frog used in flower arrangement. A metal mold prepared by micro-machine techniques may also be used as an object on which the film is put. The film is allowed to stand under heating to a high temperature for a few hours, and then cooled to prepare a film with many cavities in the form of a micro-container having the depth of from 50 to 500 µm and the caliber of from 20 to 800 µm.

For filling a drug into the micro-container-like cavities formed on the film, two ways of the solid-phase method and the liquid-phase method may be used. In the solid-phase method, a drug and an adhesive are mixed and then the resulting mixture is filled into the micro-container-like cavities at a fixed amount under the solid condition. In the liquid-phase method, an adhesive is injected into the cavities by means of a solid-phase method, and a drug solution is injected into the cavities by a microinjector.

Then, the adhesion site-controlling layer (a film made of an enteric polymer) is provided so as to cover the upper part of the micro-container-like cavities. The adhesion site-controlling layer and the film having micro-container-like cavities may be adhered to each other by previously applying an adhesive on the adhesion site-controlling layer, and applying to the film having micro-container-like cavities filled with the drug. The adhesion site-controlling layer may be adhered to the film having micro-container-like cavities filled with the drug, by heating press methods, when the drug is heat-resistant.

The resulting film, which has many cavities filled with the drug and of which the cavities are covered with the adhesion site-controlling layer, is cut into small pieces each having a cavity to prepare the formulations in the second embodiment of the present invention. The cutting may be carried out mechanically or by using a laser under the microscope.

The present invention will be explained more specifically by referring to the following examples. However, the scope of the present invention is not limited to the following examples.

EXAMPLES

Example A

Materials

A solution of G-CSF (500 µg mL$^{-1}$) was obtained from Kirin Brewery Co., Ltd (Tokyo, Japan). Hydroxypropylmethylcelloulose phthalate (HP-55) was obtained from Shinetsu Chemical Industry Co. Ltd. (Tokyo, Japan). Eudragit S100 and L100 (Rohm Pharm, Darmstadt, Germany) were obtained through Higuchi Inc. (Tokyo, Japan). Carboxyvinyl polymer (Hiviswako 103), etylcellulose (EC, 10 cp) and triethyl citrate were obtained from Wako Pure Chemical Industries, Ltd. (Osaka, Japan). Polyoxyethylated, 60 µmol, castor oil derivative (HCO-60) was obtained from Nikko Chemicals Co., Ltd (Tokyo, Japan). Polyethylene glycol (PEG) 400, Sudan black, saccharose and citric acid were obtained from Nacalai Tesque Inc. (Kyoto, Japan). Fluorescein (FL), methanol and dichloromethane were obtained from Kanto Chemical Co., Ltd. (Tokyo, Japan). Magnesium silicate was obtained from Kyowa Chemical Industry Co. Ltd. (Takamatsu, Japan). Gelatin capsules (#0) were obtained from Yoshida Co., Ltd. (Himeji, Japan). Male beagle dogs (10.0–12.5 kg) used in this study and standard solid meal of commercial food (Labo D stock) were obtained from Nippon Nousan Co., Ltd. (Yokohama, Japan). Rats were obtained from SLC (Hamamatsu, Japan). All other materials used were of reagent grade and were used as received.

Preparation of GI Mucoadhesive Delivery System

The backing layer (protecting layer) was prepared by a casting/solvent evaporation technique from plasticizer-containing EC Solution. Plasticized polymer solution (11%, W/v) was prepared by dissolving 550 mg of EC in 5 ml of the mixture of methylene chloride and methanol (4:1) and adding 150 mg of triethyl citrate to plasticize EC. To prepare the test films for the retention/transit in the GI tract of rats, 3.5 mg of sudan black was added to the mixture. The plasticized EC solution was casted over a Teflon plate, 10×10 cm, and the solvent was evaporated at 6° C. for 12 h. After removed from the plate, the same size of drug-carrying layer, cellulose membrane, was attached by a thermal bonding at 80° C. Thereafter, the backing layer having drug-carrying layer was cut to 1.0×10.0 cm. The thickness of the EC film itself was 48.3±2.7 µm, and the total thickness was 115.3±0.9 µm.

The pH-sensitive surface layer (adhesive site-controlling layer) was also prepared by the same method from enteric polymer, HP-55, Eudragit L100 and S100, respectively. Namely, 550 mg of HP-55 and 50 µl of triethyl citrate were dissolved with 10 ml of methylene chloride and methanol (4:1) mixture. Similarly, 550 mg Eudragit L100 or Eudragit S100 was dissolved with 10 ml of the methylene chloride and methanol (1:1) mixture with the addition of 100 µl of triethyl citrate. Each solution was casted on a Teflon plate, 10×10 cm, and pH-sensitive film was prepared at 6° C. for 12 h. After removed from the plate, pH-sensitive film was cut to 1.0×10.0 cm. The thickness of the enteric films were 39.0±2.5 µm for HP-55, 36.3±2.2 µm for Eudragit L100 and 37.7±2.2 µm for Eudragit S100. The mucoadhesive glue was prepared by mixing 0.8 g of Hiviswako 103, 250 µl of PEG 400 and 2 ml of water. After knitting well, the glue was uniformly spread on the surface of pH-sensitive surface layer.

The drug loading was performed as follows; At first, the drug-carrying layer was wetted with 400 µl of solution containing citric acid (100, 150 or 200 mg) and HCO-60 (50 or 100 mg) and was dried well at 50° C. for 2 h. Thereafter, a drug solution was loaded onto the drug-carrying layer. For FL study, 200 µl of FL solution, 150 mg/ml, was loaded. For G-CSF study, 180 µl or 250 µl of G-CSF solution of which concentration was 500 µg/ml was loaded. After the sheet was dried well for 12 h in a refrigerator, the pH-sensitive surface layer was attached to the drug-carrying layer with the aid of Hiviswako glue. The three layered film was cut into small pieces, 3.0×3.0 mm, and the small films were treated with micro-pulverized stearic acid and magnesium silicate to cover the edges of the films and to prevent the sticking of the films with each other. Finally, the films were filled into a #0 Hp-55 capsule with the addition of pulverized sucrose as an excipient. HP-55 capsule was prepared as follows. HP-55 was dissolved with methylene chloride and methanol (4:1) mixture. The obtained 4.0 w/v % solution was filled in a #0 gelatin capsule body and cap, respectively. After evaporation, H P-55 cap and body were obtained by dissolving gelatin layer.

Pharmacokinetic Study in Beagle Dogs

Three adult male beagle dogs were fasted overnight for 12 h in each experiment, although free access to water was allowed. However, during the course of the experiment, water was not given until 4 h after the test preparation was administered. Each dog received an oral administration of one test capsule in all studies. At 4 h after administration, a solid meal of commercial food, 450 g, and water were given. No additional food was given during the study. All the experiments were carried out at the same time of the day to exclude the influences by circadian rhythm. The administration was done at 10:30 A.M. with 20 ml of water. At 30 min before drug administration, a control blood sample (0.5 ml) was removed from the jugular vein. Each dog received one capsule which contained 30 mg of FL, or 125 μg of G-CSF. After oral administration of the test preparation, 0.5 ml of the blood samples were collected from the jugular vein at 0, 1, 2, 3, 4, 5 and 6 h for FL study and at 0, 1, 1.5, 2, 3, 4, 6, and 8 h for G-CSF study. Blood samples for the ELISA assay of G-CSF were collected in EDTA. The plasma fraction for FL assay or serum fraction for G-CSF assay was obtained by centrifuging the blood samples at 12,000 rpm for 5 min. These plasma and serum samples were immediately frozen in a freezer at −80° C. until analyzed. One week later, iv solution of FL or G-CSF was injected to the same dogs. The concentrations of the test solution were 1.0 mg/ml for FL and 500 μg/ml for G-CSF. The iv does were 10 mg for FL and 125 μg/kg for G-CSF, respectively. After administration, blood samples were collected at 0, 5, 10, 20, 30, 40 min, 1 and 2 h. The plasma samples were also stored at −80° C. until analysis.

Pharmacodynamic Study of G-CSF in Beagle Dogs

The test GI mucoadhesive delivery system containing 125 or 90 μg of G-CSF was orally administered to the same beagle dogs two weeks later and 0.5 ml of the blood samples were collected from the jugular vein at 0, 1, 2, 3, 4, 5, 6, 8, 10 and 12 h. Just after the last blood sampling, all the blood samples were used for the analysis of total white blood cell (WBC) count. In addition, the blood sample was also collected in the next morning, at 24 after administration and WBC count was measured.

Determination of retention and transit of films in the rat GI tract

Male Wistar rats weighing from 300 to 350 g were allowed to fast for 12 h before the experiments. Water was allowed ad libitum. Under light ether anesthesia, the abdominal incision was performed and ten pieces of the test films of which size was 1.0×2.0 mm were administered into the duodenum through a cut on the stomach near the pylorus. To detect the small films in the GI tract, the backing layer of the film was stained with black dye, sudan black. After abdominal suture, each rat was left in a cage. At 1, 2, 3, 4, 5 and 6 h after administration, the rats were sacrificed. The stomach and the entire length of the small intestine were isolated and both the stomach and the small intestine were spread out on a sheet. The whole small intestine from pyloric sphincter to the ileo-cecal junction was divided into 5 portions and the remaining films in the GI tract were visually detected and were recorded. Thereafter, photographs were taken with a digital camera DC-3Z (RICOH Co., Ltd., Tokyo, Japan) and the image was captured and digitized using Capview software (Logitec, Tokyo, Japan) and analyzed with PhotoDeluxe software (Adobe). Photographs were printed out using a digital color printer (SONY, Tokyo, Japan).

ASSAY METHOD

Plasma FL Concentration

The FL concentration in the plasma was determined according to a spectrophotofluorometric method. To 20011 of dog plasma sample, 0.5 ml of methanol was added. After mixing well, the resulting mixture was centrifuged at 12,000 rpm for 5 min. To the supernatant, 1 ml of 0.1 N—NaOH solution and 2 ml of distilled water were added and the fluorescence intensity was measured using a Shimadzu RF-500 spectrophotofluorometer with an excitation wavelength of 468 nm and an emission one of 512 nm.

Enzyme-Linked Immunosorbent Assay (ELISA) for G-CSF

Serum G-CSF concentrations were measured in an enzyme-linked immunosorbent assay method as follows. After 100 μl of protein solution was added to each well of flat-bottomed 96-well plate, 100 μl of the serum sample or G-CSF standard solution prepared by adding the known amount of G-CSF to the blank dog serum were added to each well. The 96 well plates were incubated for 3 h at room temperature. After incubation, the 96 well plates were washed with buffer. 200 μl of polyclonal antibody against G-CSF conjugated to alkaline phosphatase was added to each well and was incubated for 2 h. After washed, 50 μl of NADPH were added and were incubated for 1 h. 50 μl of buffered solution containing ethanol and INT-violet were added and were incubated for 0.5 h. After 2N sulfunic acid was added, the optical density of each well was determined using a microplate reader at 490 nm. For our assays, we used the weighted least-squares regression method coupled with third-order log-logit transformation.

Total White Blood Cell (WBC) Count

The pharmacological effects of G-CSF were evaluated by measuring circulating WBC counts. The 20 μl of the EDTA treated blood samples were used for the measurement of WBC after diluted and hemolyzed using stromatolizing agent. The stromatolized blood cells was counted using an automatic microcell counter (Sysmex F-500). Three measurements were performed with one blood sample. The WBC count is expressed as a relative value, determined by dividing the WBC count at each time point after drug administration by the respective value, namely, the pre-dosing WBC count.

Data Analysis

The following pharmacokinetic parameters were determined from the plasma drug concentration-time data. Cmax was the maximum drug concentration and Tmax was the time taken to reach Cmax and these values were obtained as measured values. The area under the plasma or serum drug concentration-time curve (AUC) and the area under the first-moment curve (AUMC) after i.v. and oral administrations were calculated using the linear trapezoidal rule up to the last measured drug concentration. The mean residence time (MRT) after oral administration was calculated by AUMC/AUC. The extent of bioavailability (BA) was calculated from the $Dose_{i.v.}$, $AUC_{i.v.}$, and $AUC_{oral}$ by the following equation, $BA = AUC_{oral} \cdot Dose_{i.v.}/AUC_{i.v.} \cdot Dose_{oral}$.

The pharmacological availability (PA) of the oral dose of G-CSF was calculated from the following equation: $F = (AUC_{0-48,oral} \times Dose_{i.v.})/(AUC_{0-48,i.v.} \times Dose_{oral})$ Where $AUC_{0-48,oral}$ is the individual area from time zero to 48 h under the pharmacological effect-time curve of each dog who received G-CSF GI mucoadhesive delivery system or iv solution. $Dose_{iv}$ and $AUC_{0-48,iv}$ are the average dose and area from time zero to 48 h under the pharmacological effect-time curve of all dogs given G-CSF solution intravenously. As for iv administration of the G-CSF solution, pharmacological effects were measured from time zero to 48 h when the effects returned to the pre-dose level.

Statistics

All values are expressed as their as their mean±S.E. Statistical differences were assumed to be reproducible when p<0.05 (one-sided t-test).

Results

Pharmacokinetic study of GI mucoadhesive delivery system formulated with FL

To study the pharmacokinetics of FL after oral administration in GI mucoadhesive delivery system, GI mucoadhesive delivery system containing 30 mg of FL was prepared and was administered to three beagle dogs.

In this study on GI mucoadhesive delivery system, three types of pH-sensitive surface layers were used. They were HP-55, Eudragit L100 and S100. After oral administration of these three types of GI mucoadhesive delivery system, plasma FL concentration vs. time profiles were obtained as shown in FIG. 1. In the case of both HP-55 and Eudragit L100 GI mucoadhesive delivery systems, the plasma FL concentration started to increase at 1 h and 1.5 h after oral administration to dogs and reached to the peak levels, Cmax, at 2 and 3 h, respectively. However, in the case of Eudragit S100 GI mucoadhesive delivery system, there was an absorption lag-time, approximately 2 h. Thereafter, plasma FL concentration started to increase and reached to Cmax at 5 h. Noncompartmental pharmacokinetic analysis was performed with these data and the results are shown in Table I. There are not significant differences on the AUC values between HP-55 and Eudragit L100 GI mucoadhesive delivery system. However, the AUC from Eudragit S100 GI mucoadhesive delivery system was significantly smaller than the others, because there was a great absorption lag-time due to the delivery to the lower part of of the small intestine and absorption of FL did not end within 8 h after oral administration. As this study was an explorative one, blood sampling was performed by 8 h. To determine the bioavailability of FL from the three GI mucoadhesive delivery systems, FL was iv administered to the same dogs and the results are also shown in FIG. 1. By comparing to the AUC value obtained after the iv injection of the same amount of FL, the bioavailability of FL from the three preparations were calculated to be 79.1±7.59%, 85.1±7.85% and 56.1±8.16%, respectively.

TABLE 1

Pharmacokinetic parameters of FL after oral administration in GI-mucoadhesive delivery systems to beagle dogs

| | Cmax (μg/ml) | Tmax (h) | AUC (μg.h/ml) | MRT (h) | BA (%) |
|---|---|---|---|---|---|
| HP-55 | 0.40 ± 0.03 | 2.33 ± 0.82 | 1.24 ± 0.12 | 3.45 ± 0.18 | 79.1 ± 7.59 |
| Eudragit L | 0.41 ± 0.04 | 3.33 ± 0.41 | 1.34 ± 0.12 | 3.38 ± 0.26 | 85.1 ± 7.85 |
| Eudragit S | 0.40 ± 0.02 | 5.00 ± 0.00 | 0.88 ± 0.13 | 4.32 ± 0.17 | 56.1 ± 8.16 |

Each value represents the mean ± S.E. of three subjects.

Pharmacodynamic Study of GI Mucoadhesive Delivery System Formulated with G-CSF

Figure 2:
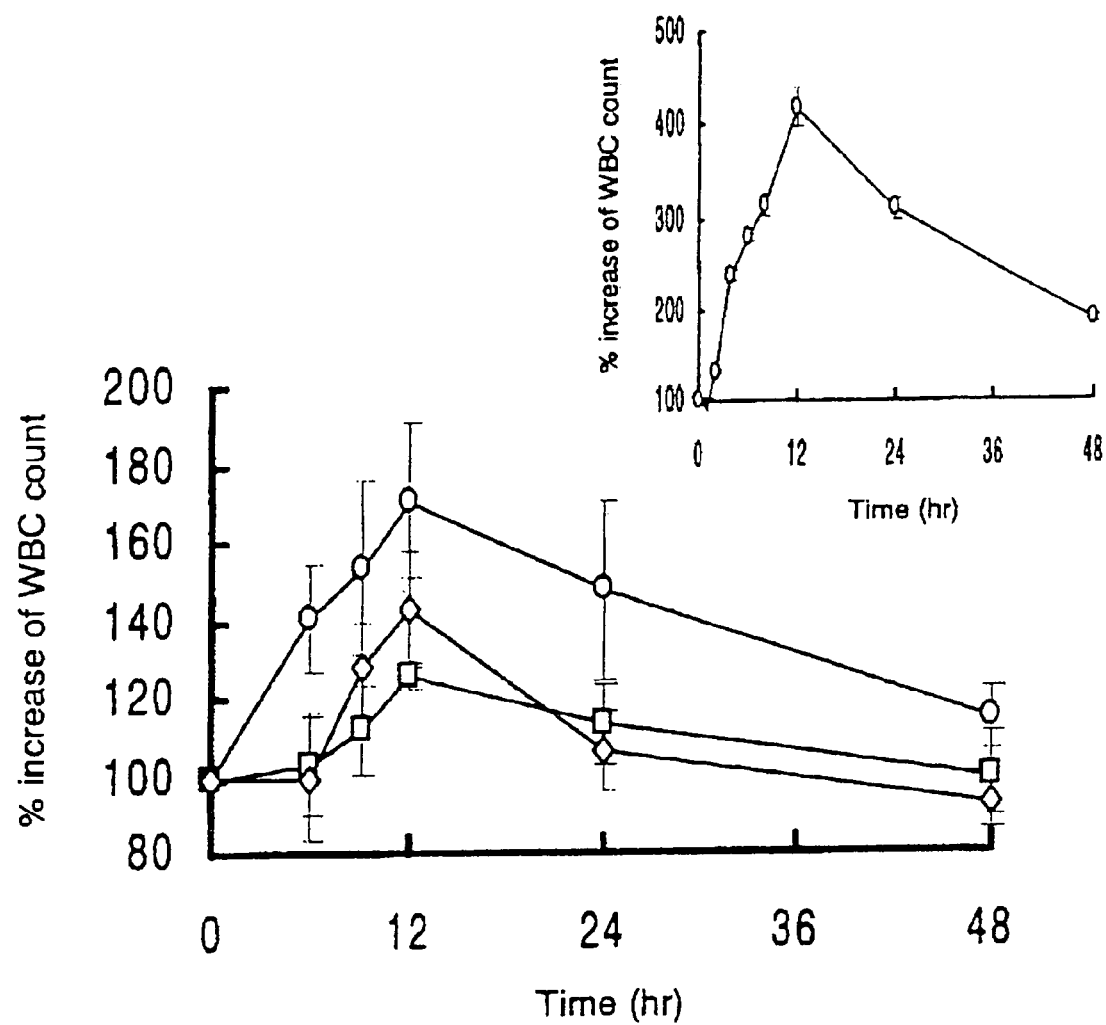
FIG. 2 shows total white blood cells (WBC) dynamics after i.v. and oral administrations of G-CSF, 125 μg, in GI-mucoadhesive delivery systems to beagle dogs. In the figure, □: HP-55$^R$ system, ○: Eudragit$^R$ L100 System, and ◇: Eudragit$^R$ S100 system. Each value represents the mean ±S.E. of three subjects.

Based on the study with FL, GI mucoadhesive delivery system was applied to a protein. G-CSF was used as a model protein, because we performed many studies on the pharmacodynamic evaluation of G-CSF formulated in oral delivery systems including colon delivery system. The 125 μg amount of G-CSF was formulated in three kinds of GI mucoadhesive delivery system and were orally administered to dogs. FIG. 2 shows the time course of the pharmacological activity of G-CSF. After administration, the WBC increased at 1.4-fold as compared to the pre-dose level in the case of HP-55 GI mucoadhesive delivery system. However, the WBC more increased, approximately 1.7-fold, in Eudragit L100 GI mucoadhesive delivery system than HP-55 GI mucoadhesive delivery system. In the case of Eudragit S100 GI mucoadhesive delivery system, the WBC did not so increase as seen in Eudragit L100 GI mucoadhesive delivery system. To determine the pharmacological availability (PA) of G-CSF from the three mucoadhesive delivery systems, the same amount of G-CSF was injected to the same dogs and the pharmacological activity of G-CSF was monitored. The inset figure shows the result. By comparing the areas under the fold increase of total WSC, the PA of the three GI mucoadhesive delivery systems are 5.5% for HP-55 GI mucoadhesive delivery system, 23% for Eudragit L100 GI mucoadhesive delivery system and 6.0% for Eudragit S100 GI mucoadhesive delivery system, respectively.

To test the dose-dependency of the pharmacological effect of G-CSF, 90 μg of G-CSF was formulated in Eudragit L100 GI mucoadhesive delivery system and was orally administered to the same dogs. The result is also shown in the figure. The increase of the total WBC was less than that predicted from the 125 μg dose study, and the maximum increase was 1.2 folds as compared to the pre-dose level.

Figure 3:
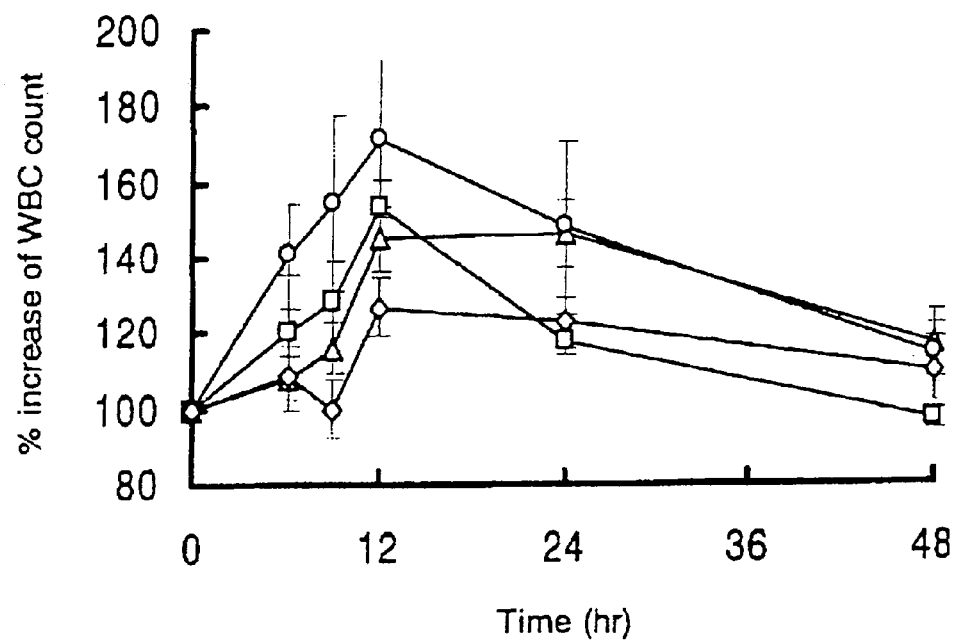
FIG. 3 shows effects of HCO-60$^R$ and citric acid on WBC dynamics after oral administration of G-CSF, 125 μg, in Eudragit$^R$ L100 GI-mucoadhesive delivery system to beagle dogs. In the figure, A: HCO-60/citric acid (100/100), □: (100/200), and ◇: HCO-60/citric acid (100/150), ○: HCO-60/citric acid (100/200), and ◇: HCO-60/citric acid (50/200). Each value represents the mean ±S.E. of three subjects.

In the GI mucoadhesive delivery system, additives such as surfactant, HCO-60, and organic acid, citric acid, were formulated. Therefore, to study the effects of additives on the pharmacological activity of G-CSF, the formulated amount of citric acid was decreased from 299 mg to 150 and 100 mg, where the amount of surfactant, HCO-60, was constant, 100 mg. As shown in FIG. 3, when the formulated amount of citric acid was decreased from 200 mg to 150 mg, the PA of G-CSF decreased. However, the PA did not significantly change by decreasing the formulated amount of citric acid from 150 mg to 100 mg. On the other hand, the enhancing effect of HCO-60 on the PA of G-CSF clearly decreased by decreasing the formulated amount of HCO-60 form 100 mg to 50 mg.

Pharmacokinetic Study of G-CSF After Oral Administration to Dogs

Figure 4:
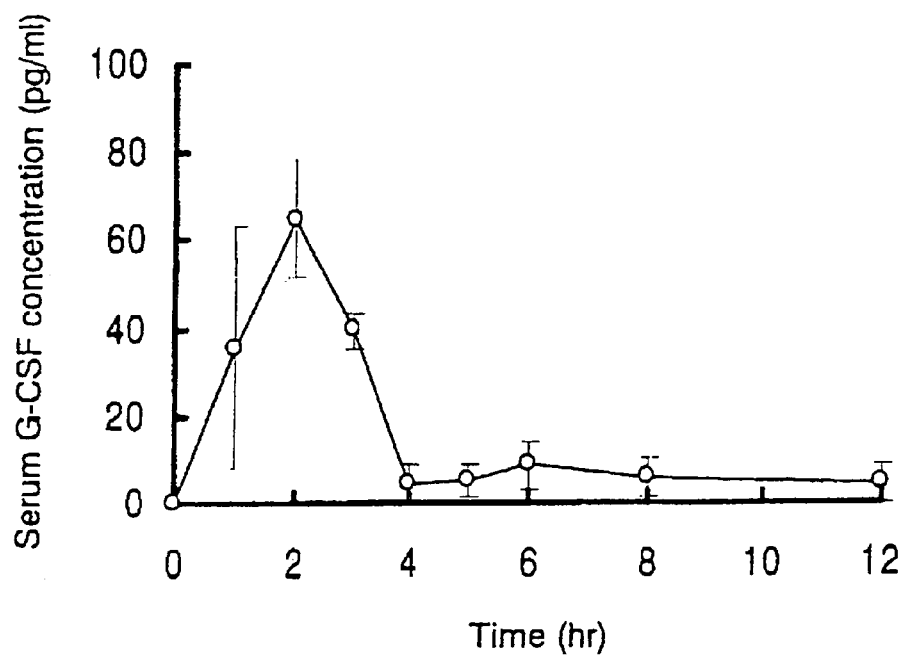
FIG. 4 shows serum G-CSF concentration-time curves after oral, 125 μg, administration of G-CSF in Eudragit$^R$ L100 GI-mucoadhesive delivery system to beagle dogs. Each value represents the mean ±S.E. of three subjects.

As Eudragit L100 GI mucoadhesive delivery system containing 125 μg of G-CSF showed the highest PA of G-CSF, the same preparations were administered to the dogs and the plasma G-CSF Levels were measured by an ELISA method. As shown in FIG. 4, plasma G-CSF levels started to increase after oral administration and reached to its peak level, 100 pg/ml, at 1 h. Thereafter, the plasma G-CSF level declined rapidly. These results strongly suggest that G-CSF was absorbed from the GI tract and entered into the systemic circulation as an intact form.

Determination of Retention and Transit of Films in the GI Tract of Rats

Figure 5A:
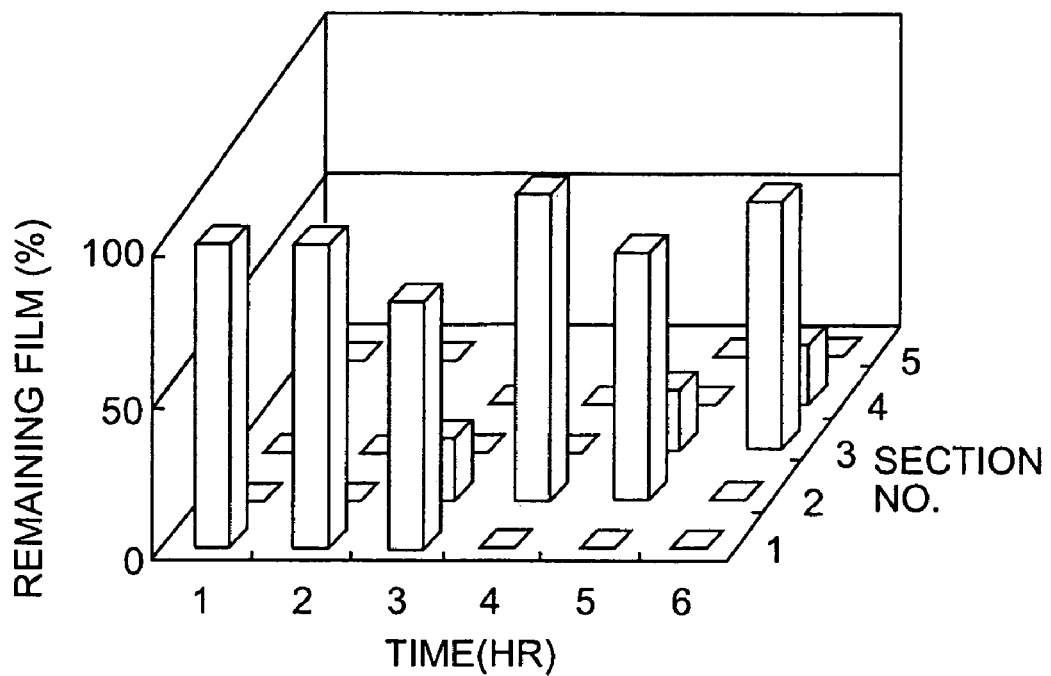
FIG. 5 shows distribution of (a) HP-55$^R$, (b) Eudragit$^R$ L100, (c) Eudragit$^R$ S100 GI-mucoadhesive delivery systems in the intestinal tract of rats after intraduodenal administration. The small intestine was divided into five sections and the length of each section was 12–15 cm.
Figure 5B:
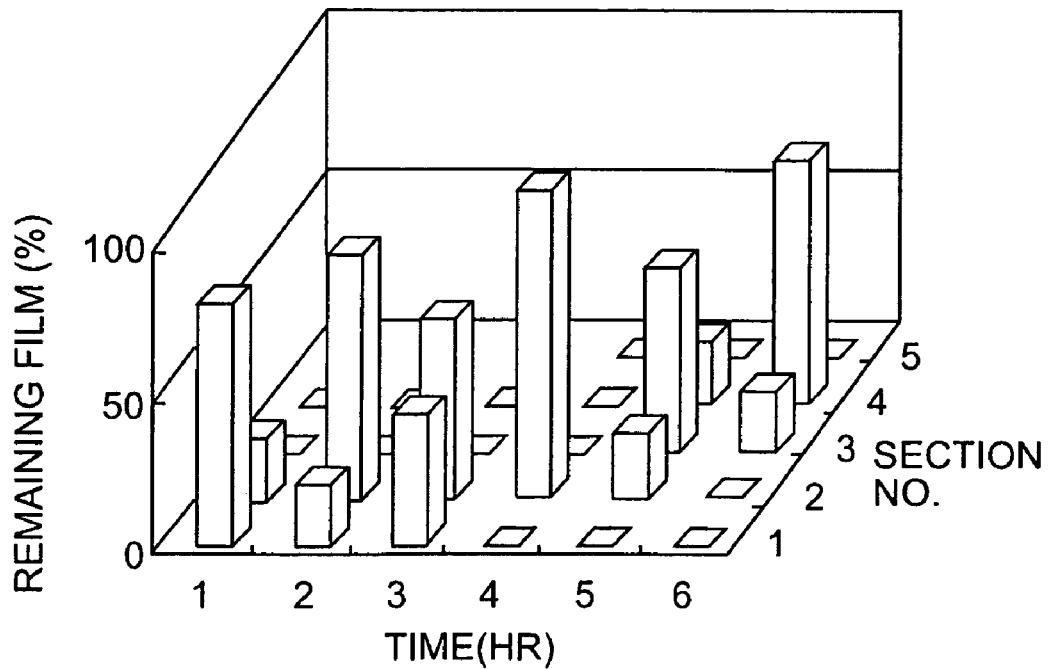
Figure 5C:
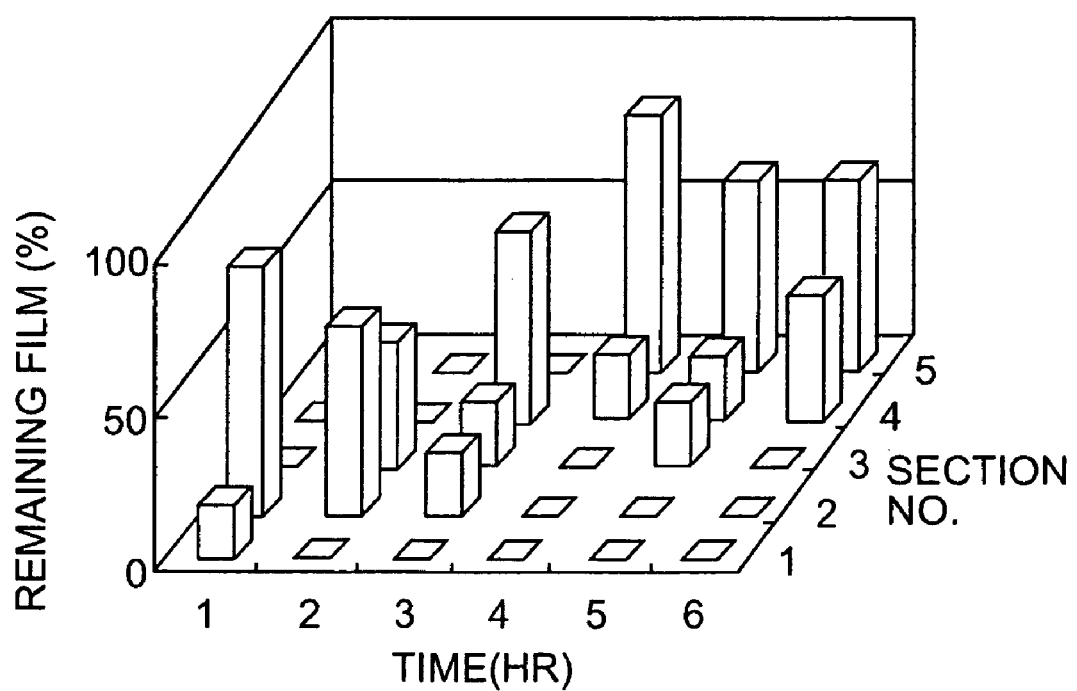

To determine the adhesive characteristics of the three GI mucoadhesive delivery systems, three kinds of smaller and colored bioadhesive films, 1.0×2.0 mm, were prepared and the test films were administered into the duodenum of rats. The retension/transit of the bioadhesive films was monitored by an abdominal incision as shown in FIG. 5. For HP-55 bioadhesive films, most of the administered films were detected in the small intestinal section #1, ie., duodenum, at 1 and 2 h after administration. In addition, the films were adhesive to the duodenum for approximately 3 h. However, at 4 h after administration, 8 of the 10 films moved to the small intestinal section #2 of the rats, and thereafter moved to the lower part of the small intestine. In the case of Eudragit L100 bioadhesive films, the films disappeared from the small intestinal section #1 within 2 h after administration and retained at section #2 for approximately 2 h. Thereafter, the films transferred to the small intestinal section #3 and #4 gradually. On the other hand, Eudragit S100 bioadhesive films transferred from section #1 to #4 gradually. It took about 3 h. Then, the films attached to the section #5 and retained there for approximately 3 h.

Example B

Example 1

An EC film (16 cm×1.6 cm) of the protecting layer (the backing layer) was applied with Hiviswako 103 glue. A tissue paper in the same size was soaked with a drug solution which was prepared by dissolving 100 µl of 1.25 mg/ml G-CSF solution, 100 mg of HCO-60 (a polyoxyethylated castor oil derivative) and 200 mg of citric acid in 200 µl of water. The tissue paper was dried and stuck to the EC film above to give the drug-carrying layer (the intermediate layer). A HP-55 film of the same size was applied with Hiviswako 103 glue, and stuck on the intermediate layer to obtain the adhesion site-controlling layer (the surface layer). The resulting three layered film was cut into small pieces, 3.0×3.0 mm, coated with magnesium silicate powders at the cutting face, and filled into a HP-55 capsule. Lactose was filled into the empty space to give an oral patch DDS formulation.

Example 2

An oral patch DDS formulation was prepared in a similar manner to that in Example 1 except that 100 mg of ursodeoxycholic acid and 2,000 units of aprotinin (an inhibitor of hydrolytic enzymes) were added to the drug solution in preparing the drug-carrying layer (the intermediate layer).

Example 3

A gelling drug-carrying layer (the intermediate layer) was prepared first. Indinavir (100 mg) was mixed with 0.8 ml of water and 100 µl of polyethylene glycol 400, and added with 300 mg of Hiviswako 103. The resulting mixture was thoroughly kneaded to give a glue. An EC film (the backing layer) of the same size as that in Example 1 was applied with the indinavir-containing glue. A HP-55 film was stuck as a surface layer film. After that, the magnesium silicate treatment was performed in a similar manner to that in Example 1, and the resulting film and an appropriate amount of lactose were filled into two HP-55 enteric capsules of Size No. 0 to give an oral patch DDS formulation of indinavir.

Example 4

An oral patch DDS formulation of indinavir was prepared in a similar manner to that in Example 3 except 200 mg of cyclosporine which is an inhibitor of P-gp transporter was added to the drug solution in preparing the drug-carrying layer (the intermediate layer).

Example 5

Ethylcellulose (EC)(550 mg) and 50 µl of triethyl citrate were dissolved in 5 ml of a mixture of methylene chloride and methanol (4:1). The resulting solution was poured onto a Teflon plate of 10 cm×10 cm, and the solvent was evaporated to form an EC film. The EC film was put on a metal mold having projections of 200 µm maximum diameter and 80 µm height, and pressed at 175° C. for 10 minutes. The film was then cooled to room temperature to form an EC film having the micro-container form. G-CSF (100 µl) as the drug, 50 mg of HCO-60 (a polyoxyethylated castor oil derivative) and 200 mg of citric acid were dissolved in 1 ml of water to prepare a drug solution. The drug solution was lyophilized, and the powdery drug was put on the EC film having the micro-container form and was uniformly filled into the micro-containers with a stainless spatula. The powder remaining on the EC plate was swept away with a stainless blush. In order to prepare a surface layer film of HP-55 which is, an enteric polymer, 300 mg of HP-55 and 50 µl of triethyl citrate were dissolved in 10 ml of a mixture of methylene chloride and methanol (4:1). The resulting solution was poured onto a Teflon plate 15×15 cm, and the solvent was evaporated to form a HP-55 film. As a glue for the adhesion, 0.8 g of Hiviswako 103, 2 ml of distilled water and 250 µl of polyethylene glycol 400 were stirred in a mortar with a pestle. The glue for the adhesion was spread on the HP-55 film and stuck to the EC film having micro-containers filled with the drug. Under the microscope, the resulting layered film was cut around the micro-containers into squares about 500×500 micron or circles about 500 micron in diameter to give ununiform microcapsule formulations having three layered structure. Cutting was performed by laser using UV laser marking machine LYH-100AA (Ushio Electronics Co.) under YAG laser 4 times high-modulated wave, wave length of 266 nm, beam wide of about 30 µm and output of 105 mV×0.77 seconds in a way that the description character "0" is traced.

Example 6

According to a conventional method (Ohyama Takao, et al., Ishoku [Transplantation], vol. 34, No. 4, pp. 174–185, 1999), Langerhans islet is obtained from rat pancreas. A microinjector is filled with the pancreatic Langerhans islet suspended in a 0.1% carboxymethylcellulose solution. Under the microscope, the pancreatic Langerhans islet is injected into micro-containers on an EC film prepared by a similar manner to that in Example 5 with the microinjector. A HP-55 film is prepared by a similar manner to that in Example 5. Hiviswako 103 glue is spread on the HP-55 film and stuck to the EC film of which the micro-containers are filled with the viable cells. Under the microscope, the resulting layered film is cut around the micro-containers into squares about 500×500 micron or circles about 500 micron in diameter to give ununiform microcapsule formulations having three layered structure.

Test Example 1

Evaluation of in Vivo Bioavailability Method

Beagle dogs were subjected to oral administration of the oral patch DDS formulation prepared in the aforementioned Example 1 to 4. After the administration, the circulating blood was collected with time and the white blood cell count in the circulating blood was detected as an indicator of the efficacy of the drug in the cases using the G-CSF formulations. The dose of the G-CSF formulations and the indinavir formulations were 125 µg/dog and 100 mg/dog, respectively. The beagle dogs were male adults weighing from 10 to 11 kg and treated under fasting conditions.

The result in the therapeutic and pharmacological test of the G-CSF formulations is shown in Table 2 below.

TABLE 2

White blood cell count after the administration

|  | Before drug administration | 6 hr | 12 hr | 24 hr | 48 hr |
| --- | --- | --- | --- | --- | --- |
| G-CSF solution | 100 | 105 | 103 | 97 | 106 |
| G-CSF formulation of Example 1 | 100 | 111 | 132 | 130 | 108 |
| G-CSF formulation of Example 2 | 100 | 120 | 141 | 139 | 109 |

The G-CSF solution is a formulation of a commercial G-CSF injection filled in an enteric capsule made of HP-55.

The white blood cell count in the circulating blood of beagle dogs before administration is defined as a baseline (100%) and the change of the white blood cell count is represented as relative values.

The result in the administration of the indinavir formulations is shown in Table 3 below.

TABLE 3

Indinavir concentration in circulating plasma after oral administration (μg/ml)

|  | 0 hr | 2 hr | 4 hr | 6 hr | 8 hr | 12 hr |
| --- | --- | --- | --- | --- | --- | --- |
| Tablet | 0 | 0 | 0 | 0 | 0 | 0 |
| Formulation of Example 3 | 0 | 0.33 | 0.21 | 0.17 | 0.13 | 0.08 |
| Formulation of Example 4 | 0 | 0.58 | 0.35 | 0.27 | 0.19 | 0.11 |

Example C

A GI mucoadhesive delivery system containing interferon-α was prepared in a similar manner as in Example A except that a solution of interferon-α of 10,000,000 IU/ml was used instead of G-CSF solution and 5,000,000 IU of interferon-α (0.5 ml of solution) was administered per beagle dog. Serum interferon-α of concentrations were evaluated in a similar manner as in Example A. The obtained data are shown in Table 4 below.

TABLE 4

Serum interferon concentration(pg/ml) after administration

| 1 hr | 2 hr | 3 hr | 4 hr | 6 hr |
| --- | --- | --- | --- | --- |
| 310 ± 58 | 343 ± 61 | 107 ± 37 | 52 ± 11 | 50 ± 17 |

Example D

Ethylcellulose (EC)(550 mg) and 150 μl of triethyl citrate were dissolved in 5 ml of a mixture of methylene chloride and methanol (4:1). The resulting solution was cast on a Teflon plate of 9.0 cm×9.0 cm to form an EC film. The EC film was put on an acrylic frame of 3.0 cm×5.0 cm. 100 mg of polyacrylic acid, 1 g of HCO-60 and 2 g of citric acid were dissolved in water to prepare a solution of 10 ml of total volume. 1.5 ml of the thus-obtained solution and 0.52 ml of a solution containing 750 μg of p24 antigen and 150 μg of cholera toxin in PBS, were added. The sample was stored overnight in a refrigerator to form a film. A film prepared by Eudragit$^R$ L was adhered thereon, and then the resulting layered film was cut into 15 pieces of similar size, and each piece was further cut into 1.0 mm×1.0 mm. The cutting face was coated with magnesium silicate powders and stearic acid fine powders.

INDUSTRIAL APPLICABILITY

Gene recombinant technique has enabled large-scale manufacturing of various protein and peptide having an useful physiological activity, but their administration route is limited to injections. Concerning the QOL (quality of life) of patients, the dosage forms are preferably oral preparations. However, protein and peptide will receive hydrolytic degradation in the digestive tract lumen by gastric acid, pepsin and proteolytic enzymes from pancreas in the stomach and intestine.

According to the present invention, a water-insoluble polymer or a wax as the protecting layer prevents the attack of the proteolytic enzymes in the digestive tract lumen. In addition, the adhesive (such as polyacrylate polymer) contained in the drug-carrying layer has inhibitory activity against hydrolytic enzymes, and can exhibit resistance to hydrolytic degradation caused by hydrolytic enzymes existing on the mucosal membrane of the digestive tract. Moreover, formulation of various hydrolytic enzyme inhibitors enables to retain the effect of the drug stronger and longer.

Furthermore, the bioavailability of the drug that is excreted again to the digestive tract after absorption can be improved. Cyclosporine and saquinavir, protease inhibitors of anti-AIDS agents, are considered to exhibit low bioavailability because of re-excretion to the digestive tract by P-gp expressed in the epithelial cells of the digestive tract. When a P-gp inhibitor to the common preparation is formulated, efficient inhibition cannot be achieved at the drug absorbing site since the preparation moves downward the digestive tract. By formulating the P-gp inhibitor in the orally available patch-type DDS formulation of the present invention, it becomes possible to retain an excretive transporter inhibitor at an adhesion site over a long period of time, and to improve the bioavailability of the drug.

In addition, antigens orally-administered cannot be fully absorbed, and can not achieve satisfactory immunization. According to the present invention, oral vaccines can also be developed which achieve an efficient absorption of antigens and improve an efficiency of immunization.

The invention claimed is:

1. An oral formulation for gastrointestinal drug delivery which comprises an adhesion site-controlling layer for attaching the formulation to a selected site in the intestines, a drug-carrying layer containing a drug and an adhesive to attach the drug containing layer to the selected site in the intestines when the adhesion site-controlling layer dissolves at the selected site in the intestines, and a protecting layer structured and arranged for preventing digestive juice from permeating into the drug-carrying layer and the drug-carrying layer from releasing the drug through the protecting layer, the drug-carrying layer existing between the protecting layer and the adhesion site-controlling layer, the adhesion site-controlling layer is attached to the protecting layer and the adhesion site-controlling layer is a film made of an enteric polymer, and the adhesion site-controlling layer contains a plasticizer.

2. The oral formulation for gastrointestinal drug delivery according to claim 1 wherein each of the adhesion site-controlling layer, the drug-carrying layer and the protecting layer is in the form of film, and said three layers are laminated.

3. The oral formulation for gastrointestinal drug delivery according to claim 2 wherein each of the adhesion site-controlling layer, the drug-carrying layer and the protecting layer has a thickness of from 20 to 100 μm.

4. The oral formulation for gastrointestinal drug delivery according to claim 1 wherein the protecting layer is in hemispherical form forming an inner space and an opening part, and the drug-carrying layer exists in the inner space of the protecting layer in said hemispherical form, and wherein the adhesion site-controlling layer covers the opening part of the protecting layer in said hemispherical form.

5. The oral formulation for gastrointestinal drug delivery according to claim 4 wherein the hemisphere has an inside depth from 50 to 500 μm, the opening part of the hemisphere has an inside diameter of from 20 to 800 μm, and each of the protecting layer and the adhesion site-controlling layer has a thickness of from 20 to 100 μm.

6. The oral formulation for gastrointestinal drug delivery according to claim 1 wherein the drug-carrying layer is a porous sheet substrate soaked with a drug, or a sheet or a film of a gel or a wax which contains a drug.

7. The oral formulation for gastrointestinal drug delivery according to claim 1 wherein the drug-carrying layer further contains one or more ingredients selected from the group consisting of absorption promoters, protease inhibitors and transporter inhibitors.

8. The oral formulation for gastrointestinal drug delivery according to claim 1 wherein the protecting layer is a film or a capsule, each of said film or capsule being composed of at least one of a water-insoluble polymer and a wax.

9. The oral formulation for gastrointestinal drug delivery according to claim 1 wherein the drug is a physiologically active protein or peptide.

10. The oral formulation for gastrointestinal drug delivery according to claim 1 wherein the drug is G-CSF, interferon or indinavir.

11. An oral capsule formulation which is prepared by filling the formulation according to claim 1 in a capsule.

12. The oral capsule formulation according to claim 11 which is an enteric capsule.

13. An oral capsule formulation which is prepared by filling the formulation according to claim 2 in a capsule.

14. An oral capsule formulation which is prepared by filling the formulation according to claim 4 in a capsule.

15. An oral capsule formulation which is prepared by filling the formulation according to claim 6 in a capsule.

16. An oral capsule formulation which is prepared by filling the formulation according to claim 7 in a capsule.

17. An oral capsule formulation which is prepared by filling the formulation according to claim 8 in a capsule.

18. An oral capsule formulation which is prepared by filling the formulation according to claim 9 in a capsule.

19. An oral capsule formulation which is prepared by filling the formulation according to claim 10 in a capsule.

20. The oral formulation for gastrointestinal drug delivery according to claim 1 wherein the drug-carrying layer is sealed between the adhesion site-controlling layer and the protecting layer to prevent leaking of the drug.

21. The oral capsule formulation according to claim 13 which is an enteric capsule.

22. The oral capsule formulation according to claim 14 which is an enteric capsule.

* * * * *